United States Patent
Chow

(10) Patent No.: US 9,072,447 B2
(45) Date of Patent: Jul. 7, 2015

(54) DETERMINATION OF HEMODYNAMIC INTOLERANCE OF VENTRICULAR PACING

(75) Inventor: Theodore Chow, Saratoga, CA (US)

(73) Assignee: Medtronic, Inc., Minneapolis, MN (US)

( * ) Notice: Subject to any disclaimer, the term of this patent is extended or adjusted under 35 U.S.C. 154(b) by 1363 days.

(21) Appl. No.: 12/476,713

(22) Filed: Jun. 2, 2009

(65) Prior Publication Data
US 2009/0299428 A1 Dec. 3, 2009

Related U.S. Application Data

(60) Provisional application No. 61/130,599, filed on Jun. 2, 2008.

(51) Int. Cl.
A61N 1/362 (2006.01)
A61B 5/0464 (2006.01)
A61N 1/365 (2006.01)

(52) U.S. Cl.
CPC ............ *A61B 5/0464* (2013.01); *A61N 1/3627* (2013.01); *A61N 1/36592* (2013.01)

(58) Field of Classification Search
CPC .................. A61N 1/3627; A61N 1/36592
USPC .......................................................... 607/17
See application file for complete search history.

(56) References Cited

U.S. PATENT DOCUMENTS

| | | | |
|---|---|---|---|
| 5,042,497 A * | 8/1991 | Shapland | 600/509 |
| 6,922,585 B2 | 7/2005 | Zhou et al. | |
| 6,942,622 B1 | 9/2005 | Turcott | |
| 7,130,689 B1 | 10/2006 | Turcott | |
| 7,177,686 B1 * | 2/2007 | Turcott | 607/23 |
| 7,206,636 B1 | 4/2007 | Turcott | |
| 2004/0215262 A1 | 10/2004 | Ferek-Petric | |
| 2008/0183231 A1 | 7/2008 | Sathaye et al. | |

FOREIGN PATENT DOCUMENTS

EP 1 870 129 A1 12/2007

OTHER PUBLICATIONS

Response dated May 2, 2011, from European application No. 09759230.7, 6 pp.
Search Report and Written Opinion from corresponding PCT Application Serial No. PCT/US2009/045952 mailed Sep. 14, 2009 (12 pages).
Mary A. Woo et al., "Comparison of Four Methods of Assessing Heart Rate Variability in Patients With Heart Failure", American Journal of Critical Care, Jan. 1996, vol. 5, No. 1, pp. 34-41.
International Preliminary Report on Patentability from corresponding PCT Application Serial No. PCT/US2009/045952 dated Jun. 4, 2010 (10 pages).

(Continued)

*Primary Examiner* — Eric D. Bertram
(74) *Attorney, Agent, or Firm* — Shumaker & Sieffert, P.A.

(57) ABSTRACT

In some examples, this disclosure describes techniques for assessing hemodynamic intolerance of ventricular pacing. A method comprises sensing a parameter indicative of autonomic tone during a first period in which a medical device delivers ventricular pacing to a patient, sensing the parameter indicative of autonomic tone during a second period in which the medical device does not deliver ventricular pacing to the patient, and assessing a level of change in autonomic tone in the patient induced by ventricular pacing based on values of the sensed parameter during the first and second periods.

44 Claims, 8 Drawing Sheets

(56) References Cited

OTHER PUBLICATIONS

Response to Written Opinion from corresponding PCT Application Serial No. PCT/US2009/045952 filed on Apr. 2, 2010 (12 pages).
European Office Action from corresponding Application Serial No. 09 759 230.7-2305 dated Mar. 30, 2012 (4 pages).
European Response filed on Aug. 6, 2012 for corresponding European Application No. 09759230.7 (6 pages).
Response to Office Action dated Aug. 5, 2014, from counterpart European Application No. 09759230.7, filed on Dec. 10, 2014, 3 pp.
Examination Report from Counterpart European Patent Application No. 09759230.7, dated Aug. 5, 2014, 5 pp.

* cited by examiner

DETERMINATION OF HEMODYNAMIC INTOLERANCE OF VENTRICULAR PACING

This application claims the benefit of U.S. Provisional Application No. 61/130,599, to Chow, entitled, "Determination of hemodynamic intolerance of ventricular pacing through an implantable cardiac pacemaker or defibrillator," and filed on Jun. 2, 2008, the entire content of which is incorporated herein by reference.

TECHNICAL FIELD

This disclosure relates to implantable medical devices and, more particularly, implantable medical devices that deliver cardiac pacing.

BACKGROUND

Cardiac pacing is delivered to patients to treat a wide variety of cardiac dysfunctions. Cardiac pacing is often delivered by an implantable medical device (IMD), which may also provide cardioversion or defibrillation, if needed. The IMD delivers such stimulation to the heart via electrodes located on one or more leads, which are typically intracardiac leads.

Patients with heart failure are often treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle, such as the left ventricle, to synchronize its contraction with that of the other, e.g., right, ventricle.

SUMMARY

In general, this disclosure describes techniques for assessing hemodynamic intolerance of ventricular pacing, such as right ventricular (RV) pacing. In patients that are hemodynamically intolerant to ventricular pacing, ventricular pacing may lead to interventricular dyssynchrony and heart failure. However, occurrence of hemodynamic intolerance is unpredictable, may take years to manifest, and may not be recognized because its symptoms are nonspecific and overlap with physical deconditioning, lung disease, and normal "old age." Therefore, a method for determining the presence of hemodynamic intolerance of ventricular pacing may provide clinical advantage.

In general, intolerance of ventricular pacing is determined by assessing a change in autonomic tone between a period of ventricular pacing and a period without ventricular pacing. In other examples, a pacing mode is selected by comparing autonomic tone during periods of pacing according to two or more pacing modes. In other examples, a value of a pacing interval, such as an A-V, V-V, A-A, RV-LV, A-RV, or A-LV interval is selected by comparing autonomic tone during periods of pacing according to two or more values for such an interval.

In one example, the disclosure is directed toward a method comprising sensing a parameter indicative of autonomic tone during a first period in which a medical device delivers ventricular pacing to a patient, sensing the parameter indicative of autonomic tone during a second period in which the medical device does not deliver ventricular pacing to the patient, and assessing a level of change in autonomic tone in the patient induced by ventricular pacing based on values of the sensed parameter during the first and second periods.

In another example, the disclosure is directed toward a system comprising a medical device that delivers ventricular pacing to a patient during a first period and does not deliver ventricular pacing to the patient during a second period, a sensor that senses a parameter indicative of autonomic tone during each of the first and second periods, and a processor that assesses a level of change in autonomic tone in the patient induced by ventricular pacing based on values of the sensed parameter during the first and second periods.

In another example, the disclosure is directed toward a medical device comprising a signal generator that delivers ventricular pacing to a patient during a first period and does not deliver ventricular pacing to the patient during a second period, a sensor that senses a parameter indicative of autonomic tone during each of the first and second periods, and a processor that assesses a level of change in autonomic tone in the patient induced by ventricular pacing based on values of the sensed parameter during the first and second periods.

In another example, the disclosure is directed toward a system comprising means for sensing a parameter indicative of autonomic tone during a first period in which a medical device delivers ventricular pacing to a patient, means for sensing the parameter indicative of autonomic tone during a second period in which the medical device does not deliver ventricular pacing to the patient, and means for assessing a level of change in autonomic tone in the patient induced by ventricular pacing based on values of the sensed parameter during the first and second periods.

In another example, the disclosure is directed toward a computer readable medium comprising instructions that cause a processor to sense a parameter indicative of autonomic tone during a first period in which a medical device delivers ventricular pacing to a patient, sense the parameter indicative of autonomic tone during a second period in which the medical device does not deliver ventricular pacing to the patient, and assess a level of change in autonomic tone in the patient induced by ventricular pacing based on values of the sensed parameter during the first and second periods.

In another example, the disclosure is directed toward a method comprising sensing a parameter indicative of autonomic tone during a first period in which a medical device delivers pacing therapy to a patient according to a first pacing mode, sensing the parameter indicative of autonomic tone during a second period in which the medical device delivers pacing therapy to the patient according to a second, different pacing mode, and selecting the first or second pacing mode for pacing therapy based on values of the sensed parameter during the first and second periods.

In another example, the disclosure is directed toward a system comprising a medical device that delivers pacing therapy to a patient according to a first pacing mode during a first period and delivers pacing therapy to the patient according to a second pacing mode during a second period, a sensor that senses a parameter indicative of autonomic tone during each of the first and second periods, and a processor that selects the first or second pacing mode for pacing therapy based on values of the sensed parameter during the first and second periods.

The details of one or more examples are set forth in the accompanying drawings and the description below. Other features, objects, and advantages will be apparent from the description and drawings, and from the claims.

DETAILED DESCRIPTION

Figure 1:
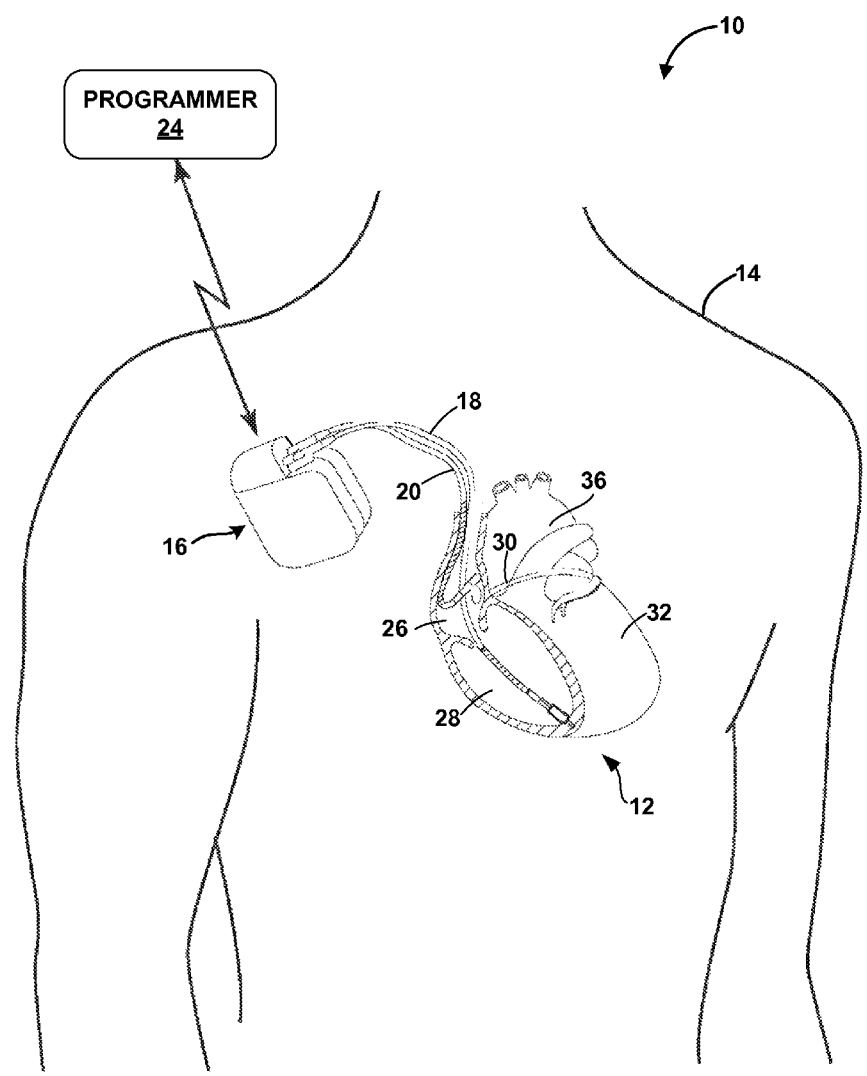
FIG. 1 is a conceptual diagram illustrating an example therapy system comprising an implantable medical device

In some examples, this disclosure describes techniques for assessing hemodynamic intolerance of ventricular pacing, such as right ventricular (RV) pacing. In patients that are hemodynamically intolerant to ventricular pacing, ventricular pacing may lead to ventricular dyssynchrony and heart failure. Ventricular dyssynchrony may refer to conduction delays that disturb the synchronous beating of the ventricles so that they pump less efficiently. Ventricular dyssynchrony has been shown to have a number of deleterious effects on cardiac function and may result in diminished stroke volume.

Occurrence of hemodynamic intolerance is unpredictable, may take years to manifest, and may not be recognized because its symptoms are nonspecific and overlap with physical deconditioning, lung disease, and normal "old age." Therefore, a method for determining the presence of hemodynamic intolerance of ventricular pacing may have clinical advantage.

A change in autonomic tone in response to ventricular pacing may provide an early indication of hemodynamic intolerance. More specifically, an increase in sympathetic tone and/or a decrease in parasympathetic tone in response to ventricular pacing may provide an indication of hemodynamic intolerance. A shift in autonomic tone from parasympathetic predominance to sympathetic predominance may be associated with congestive heart failure (CHF) mortality and sudden death from ventricular arrhythmia. Therefore, it follows that a shift in autonomic tone in response to ventricular pacing may provide an indication of hemodynamic intolerance.

Heart rate variability (HRV) is one measure of autonomic tone. Low HRV indicates sympathetic predominance, while high HRV indicates parasympathetic predominance. A sensor may monitor a signal indicative of HRV and/or another parameter indicative of autonomic tone both during a period of ventricular pacing as well as during a period of no ventricular pacing. If the autonomic tone measurement suggests a significant shift towards sympathetic tone during ventricular pacing, it may be determined that the patient does not tolerate ventricular pacing hemodynamically.

The sensor that detects a signal indicative of autonomic tone may be coupled to the medical device that delivers the ventricular pacing therapy. As one example, one or more electrodes on a lead coupled to the medical device may function as sensors and monitor an electrical signal indicative of autonomic tone. The medical device may store an indication of the level of change in autonomic tone induced by ventricular pacing based on values of the sensed parameter. The stored indication may later be transmitted to a clinician, e.g., via a clinician programmer. In some cases, the medical device automatically transmits a notification to a user, e.g., the patient or clinician, if the detected change in autonomic tone is significant, e.g., exceeds a threshold value. In some examples, the medical device automatically modifies therapy delivery based on the assessment of autonomic tone. As one example, the medical device may decrease the usage of ventricular pacing by, for example, increasing an atrioventricular (A-V) delay or interval.

In some examples, an indication of autonomic tone is compared between two or more pacing modes. The two or more pacing modes may include a mode that provides ventricular pacing and a mode that does not provide ventricular pacing. The two or more modes may include modes that provide different amounts or types of ventricular pacing. Different types of ventricular pacing may include RV-only, LV-only, or biventricular pacing. Each pacing mode may specify which chambers are sensed and/or which chambers are paced. Common pacing modes include DDD, VVI and AAI, which may be rate-responsive, e.g., DDD(R), VVI(R) and AAI(R).

An atrial-based pacing mode, e.g., AAI(R), may pace in one or both of the left and right atria. In some examples, an atrial-based pacing mode may provide back-up ventricular pacing. One example of such an atrial-based pacing mode with back-up ventricular pacing is Managed Ventricular Pacing (MVP) commercially available from Medtronic Inc. of Minneapolis, Minn. A dual chamber pacing mode, e.g., DDD(R), may pace one or both of the left and right atria and one or both of the left and right ventricles. In some examples, an atrial-based or dual chamber pacing mode is selected based on a comparison of autonomic tone during periods of pacing according to each of the modes.

Atrial-based pacing modes may result in longer intervals between a paced or intrinsic atrial depolarization and the subsequent intrinsic ventricular depolarization due to the intrinsic atrioventricular conduction of the patient. In some cases, this increased interval may have a negative impact on autonomic tone, e.g., increase sympathetic and/or decrease parasympathetic tone, and ventricular pacing may be preferred. Furthermore, some examples may compare a CRT mode to a non-CRT mode, or a biventricular pacing mode to a single ventricular pacing mode. A comparison of levels of autonomic tone corresponding to different pacing modes may provide a basis for evaluating which pacing mode is appropriate for the patient.

Additionally, in some examples, a device may determine a value for a pacing interval, such as an A-V, V-V, A-A, RV-LV, A-RV, or A-LV interval, based on a comparison of the autonomic tone during periods of pacing according to different values for such intervals. Selection of a value for a pacing interval is distinct from selecting a pacing mode in the sense that the pacing interval defines an interval of time from an event at which a pacing pulse may be delivered, and a pacing mode specifies which chambers are sensed and/or paced.

FIG. 1 is a conceptual diagram illustrating an example therapy system 10 that may be used to monitor one or more physiological parameters of patient 14 and/or to provide therapy to heart 12 of patient 14. Therapy system 10 includes IMD 16, which is coupled to leads 18 and 20, and programmer 24. IMD 16 may be an implantable pacemaker that provides electrical signals to heart 12 via electrodes coupled to one or more of leads 18 and 20. In some examples, IMD 16 may also include cardioversion and/or defibrillation functionalities. Patient 12 is ordinarily, but not necessarily, a human patient.

Leads 18 and 20 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Right atrial (RA) lead 20 extends through one or more veins and the vena cava, and into the right atrium 26 of heart 12. RA lead 22 may be used for RA sensing and/or pacing.

Although not illustrated in FIG. 1, in some examples a cardiac therapy system may include a Left ventricular (LV) lead that extends through one or more veins, the vena cava, right atrium 26, and into the coronary sinus 30 to a region adjacent to the free wall of left ventricle 32 of heart 12. An LV lead may be used to deliver LV pacing to heart 12. As another example, LV lead 20 may be used in combination with RV lead 18 to deliver cardiac resynchronization therapy (CRT) to heart 12. CRT may be used to treat heart failure-inducted conduction disturbances and/or ventricular dyssynchrony. In some cases, CRT may help restore the mechanical sequence of ventricular activation and contraction. CRT may involve biventricular pacing, e.g., via RV lead 18 and an LV lead, to synchronize the contraction of both ventricles.

IMD 16 may trigger ventricular pacing, e.g., RV, LV, or biventricular pacing, based on atrial depolarizations sensed via RA lead 22. As another example, RA lead 22 may deliver atrial pacing, and IMD 16 may trigger ventricular pacing based on atrial-paced events. Thus, timing between the atrial and ventricular contractions can be adjusted to improve cardiac function. The delay between an atrial sensed or paced event and delivery of a pacing pulse to one or more of the ventricles may be referred to as an atrioventricular (A-V) delay or interval. In some alternative examples, therapy system 10 may include an additional lead or lead segment (not shown in FIG. 1) that deploys one or more electrodes within the vena cava or other vein, or within or near the aorta.

IMD 16 may sense electrical signals attendant to the depolarization and repolarization of heart 12 via electrodes (not shown in FIG. 1) coupled to at least one of the leads 18 and 20. In some examples, IMD 16 provides pacing pulses to heart 12 based on the electrical signals sensed within heart 12. The electrical signals sensed within heart 12 may also provide an indication of autonomic tone. The configurations of electrodes used by IMD 16 for sensing and pacing may be unipolar or bipolar. IMD 16 may also provide defibrillation therapy and/or cardioversion therapy via electrodes located on at least one of the leads 18 and 20. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art. IMD 16 may similarly deliver anti-tachycardia pacing or cardioversion in response to detecting tachycardia of ventricles 28 and 32.

In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, or other clinician, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14 or information derived from sensed physiological parameters, such as an indication autonomic tone, as described herein. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing and, optionally, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
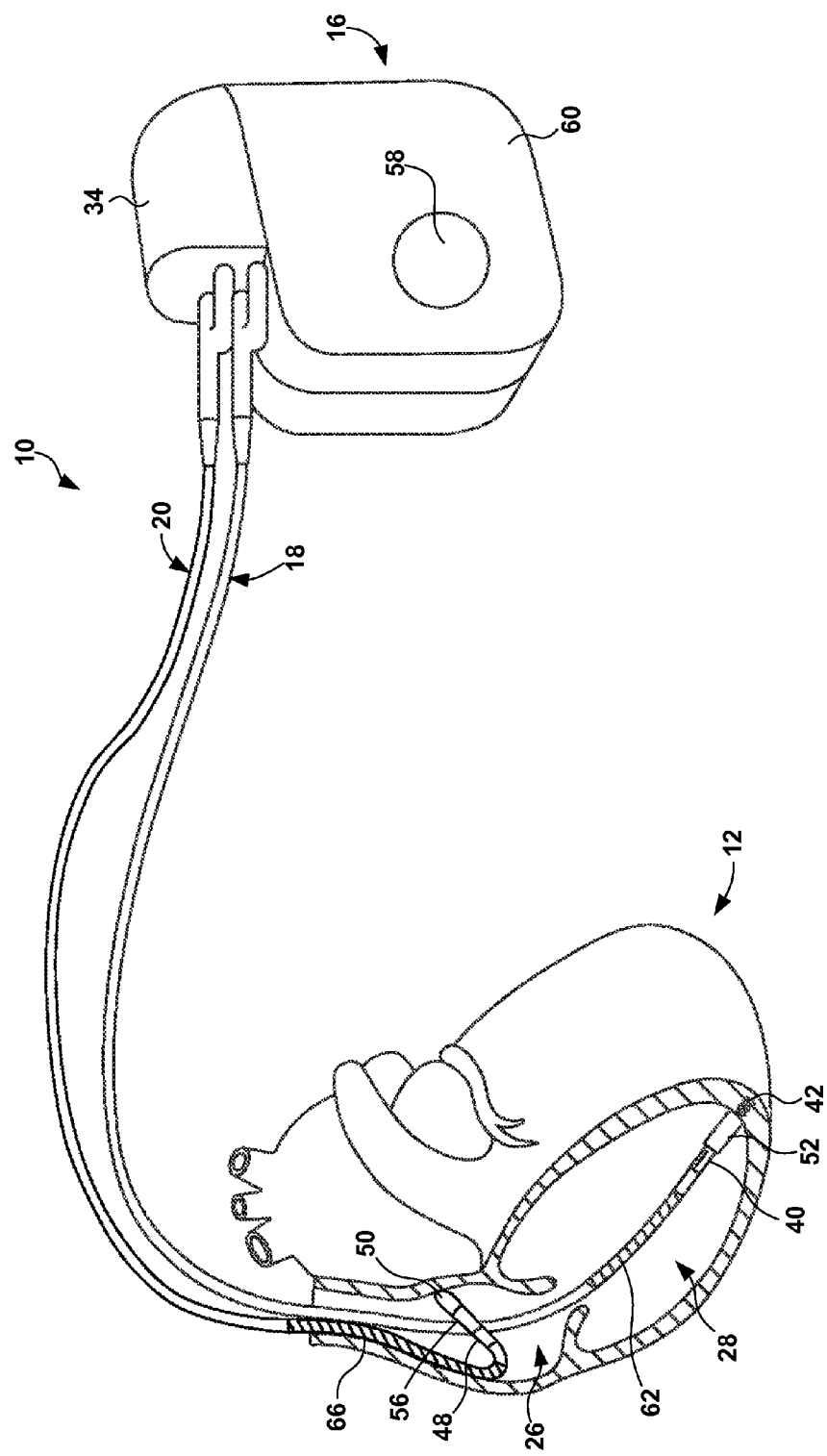
FIG. 2 is a conceptual diagram further illustrating the IMD and leads of the system of FIG. 1 in conjunction with the heart.

FIG. 2 is a conceptual diagram illustrating IMD 16 and leads 18 and 20 of therapy system 10 in greater detail. Leads 18 and 20 may be electrically coupled to a stimulation generator and a sensing module of IMD 16 via connector block 34. In some examples, proximal ends of leads 18 and 20 may include electrical contacts that electrically couple to respective electrical contacts within connector block 34 of IMD 16. In addition, in some examples, leads 18 and 20 may be mechanically coupled to connector block 34 with the aid of set screws, connection pins, snap connectors, or another suitable mechanical coupling mechanism.

Each of the leads 18 and 20 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 48 and 50 are located adjacent to a distal end of lead 22 in right atrium 26. There are no electrodes located in or near left ventricle 32 or left atrium 36 in the illustrated example, but other examples may include electrodes in left ventricle 32 and/or left atrium 36. Furthermore, other examples may include electrodes in other locations, such as the aorta or a vena cava, or epicardial or extracardial electrodes proximate to any of the chambers or vessels described herein Electrodes 40 and 48 may take the form of ring electrodes, and electrodes 42 and 50 may take the form of extendable helix tip electrodes mounted retractably within insulative electrode heads 52 and 56, respectively. In other examples, one or more of electrodes 42 and 50 may take the form of small circular electrodes at the tip of a tined lead or other fixation element. Leads 18 and 20 also include elongated electrodes 62 and 66, respectively, which may take the form of a coil. Each of the electrodes 40, 42, 48, 50, 62, and 66 may be electrically coupled to a respective one of the coiled conductors within the lead body of its associated lead 18, 20, and thereby coupled to respective ones of the electrical contacts on the proximal end of leads 18 and 20.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 senses electrical signals attendant to the depolarization and repolarization of heart 12 via electrodes 40, 42, 48, 50, 58, 62, and 66. The electrical signals are conducted to IMD 16 from the electrodes via the respective leads 18, 20 or, in the case of housing electrode 58, a conductor coupled to housing electrode 58. IMD 16 may sense such electrical signals via any bipolar combination of electrodes 40, 42, 48, 50, 58, 62, and 66. Furthermore, any of the electrodes 40, 42, 48, 50, 58, 62, and 66 may be used for unipolar sensing in combination with housing electrode 58.

In some examples, IMD 16 delivers pacing pulses via bipolar combinations of electrodes 40, 42, 48 and 50 to produce depolarization of cardiac tissue of heart 12. In some examples, IMD 16 delivers pacing pulses via any of electrodes 40, 42, 48 and 50 in combination with housing electrode 58 in a unipolar configuration. For example, electrodes 40, 42, and/or 58 may be used to deliver RV pacing to heart 12. Additionally or alternatively, electrodes 48, 50 and/or 58 may be used to deliver RA pacing to heart 12.

Furthermore, IMD 16 may deliver defibrillation pulses to heart 12 via any combination of elongated electrodes 62 and 66, and housing electrode 58. Electrodes 58, 62, 66 may also be used to deliver cardioversion pulses to heart 12. Electrodes 62 and 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. It should be understood that various other electrode and lead configurations are within the scope of this disclosure. For example, a therapy system may include epicardial leads and/or patch electrodes instead of or in addition to the transvenous leads 18 and 20 illustrated in FIGS. 1 and 2.

In addition, in other examples, a therapy system may include any suitable number of leads coupled to IMD 16, and each of the leads may extend to any location within or proximate to heart 12. Other examples of therapy systems may include two transvenous leads located as illustrated in FIGS. 1 and 2, and an additional lead located within or proximate to left ventricle 32 and/or left atrium 36. Additional examples of therapy systems may include a single lead that extends from IMD 16 into right ventricle 28, or a single lead that extends from IMD 16 proximate to left ventricle 32.

Figure 3:
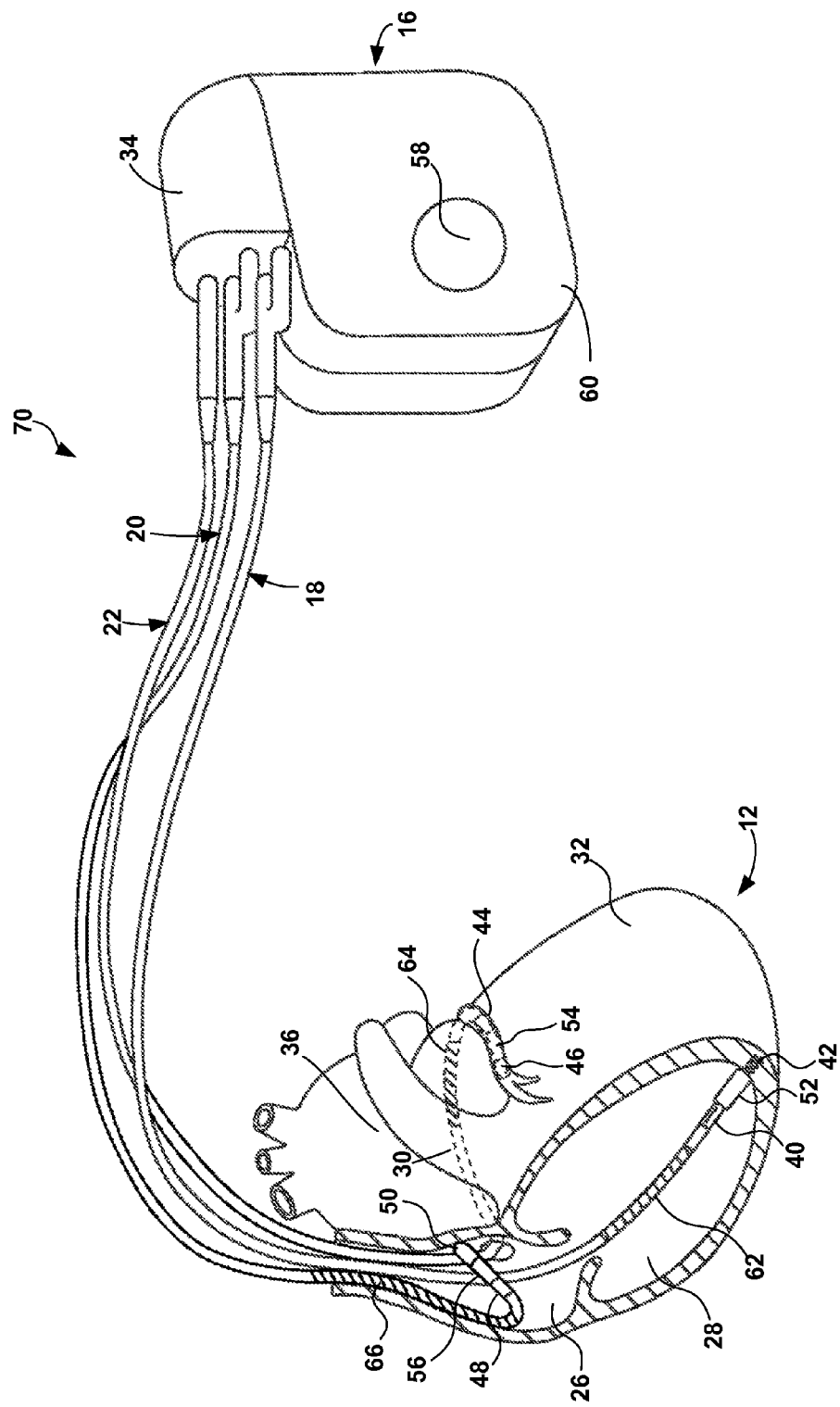
FIG. 3 is a conceptual diagram illustrating another example therapy system.

FIG. 3 is a conceptual diagram illustrating another example of therapy system 70, which is similar to therapy system 10 of FIGS. 1 and 2, but includes three leads 18, 20, 22, rather than two leads. Left ventricular (LV) lead 22 extends through one or more veins, the vena cava, right atrium 26, and into the coronary sinus 30 to a region adjacent to the free wall of left ventricle 32 of heart 12. LV lead 22 includes electrodes 44, 46 and 64, which may be configured and used in the manner described above with respect to electrodes 40, 42 and 62 of lead 18, and electrodes 48, 50 and 66 of lead 20. Electrode 46 may be retractable mounted within insulative head 54. Therapy system 70 shown in FIG. 3 may be useful for providing pacing, cardioversion and/or defibrillation pulses to heart 12 in the manner described above with respect to therapy system 10, but may additionally provide pacing, cardioversion and or defibrillation pulses to left ventricle 32.

As described above, in some examples, the LV pacing may be delivered for cardiac resynchronization therapy (CRT). CRT may involve biventricular pacing, e.g., via RV lead 18 and an LV lead, to synchronize the contraction of both ventricles. In other examples, CRT involves pacing of one of the ventricles to synchronize its contraction with the other ventricle, e.g., pacing the left ventricle 32 to synchronize its contraction with the right.

In some examples, when a clinician receives an indication that right ventricular pacing is not hemodynamically well-tolerated by patient 14, the clinician may determine that the patient should receive CRT to improve the hemodynamic performance of heart 12. In some examples, the patient may have a system such as system 10 of FIGS. 1 and 2 implanted when it is determined that RV-only pacing is not well tolerated, and the clinician may decide to implant an LV lead 22 to address the intolerance and improve the hemodynamic performance of heart 12. The clinician may explant RV lead 18, or leave RV lead 18 in place to provide a system such as system 70 illustrated in FIG. 3.

Figure 4:
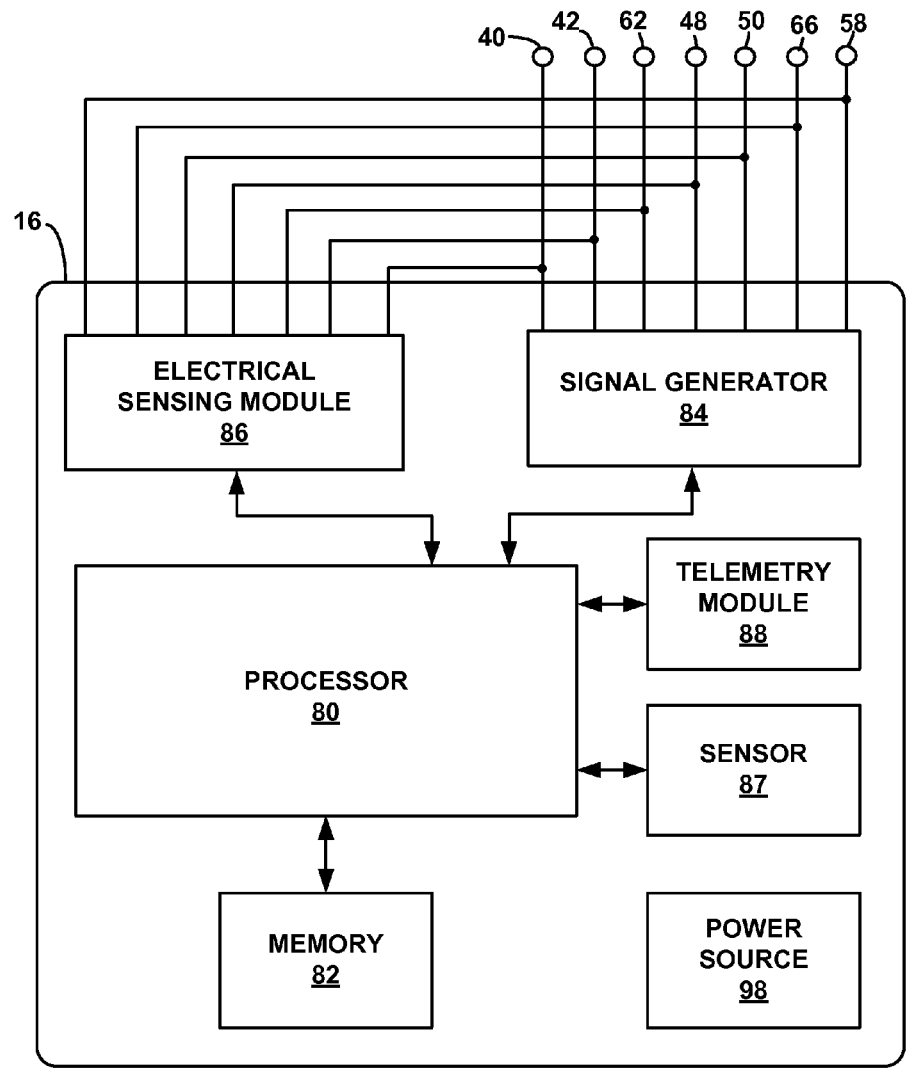
FIG. 4 is a functional block diagram illustrating an example configuration of an IMD.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. Signal generator 84 is electrically coupled to electrodes 40, 42, 48, 50, 58, 62, and 66, e.g., via conductors of the respective lead 18, 20, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 66. Signal generator 84 may deliver pacing pulses via ring electrodes 40, 48 coupled to leads 18 and 22, respectively, and/or helical electrodes 42, and 50 of leads 18 and 20, respectively. In some examples, signal generator 84 delivers pacing and, optionally, cardioversion and/or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple a signal to selected electrodes.

Electrical sensing module 86 monitors signals from at least one of electrodes 40, 42, 48, 50, 58, 62, or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chamber of heart 12, and may be configured to detect either R-waves or P-waves. In some examples, electrical sensing module 86 or processor 80 may include an analog-to-digital converter for digitizing the signal received from a sensing channel for electrogram signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Stimulation generator 84 may include pacer output circuits that are coupled, e.g., selectively by a switching module, to any combination of electrodes 40, 42, 48, 50, 58, 62, or 66 appropriate for delivery of a bipolar or unipolar pacing pulse to one or more of the chambers of heart 12. Processor 80 may control signal generator to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include A-A, V-V, RV-LV, A-V, A-RV, or A-LV interval counters, as examples. The escape interval counters may be referred to as pacing interval counters and may control the duration or value of pacing intervals.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as an atrial or ventricular fibrillation or tachycardia.

Processor 80 may also use R-wave and/or P-wave detection channels of electrical sensing module 86 to measure durations of R-R intervals, P-P intervals, P-R intervals and R-P intervals for purposes of monitoring heart rate variability. As previously stated, heart rate variability may provide an indication of autonomic tone. Processor 80 may compare values of heart rate variability recorded while signal generator 84 delivers ventricular pacing to values of heart rate variability recorded when signal generator 84 does not deliver ventricular pacing, e.g., while signal generator 84 does not output a signal. Additionally or alternatively, processor 80 may compare values of heart rate variability recorded while signal generator 84 delivers a stimulation according to a first pacing mode to values of heart rate variability recorded when signal generator 84 delivers stimulation according to a second, different pacing mode. Processor 80 may use the recorded values of heart rate variability to assess a level of change in autonomic tone in the patient induced by ventricular pacing or a level of autonomic tone attributed to a pacing mode. Memory 82 may store values indicative of heart rate variability, autonomic tone and/or a change in autonomic tone.

In general, processor 80 may assess heart rate variability and/or autonomic tone by analyzing any electrical signal sensed by electrical sensing module 86. For example, processor 80 may analyze a sensed electrogram signal or a signal derived from a sensed electrogram signal in the time and/or frequency domain. As one example, processor 80 may calculate a ratio of a high frequency component of a frequency spectrum of heart rate variability to a low frequency component of the frequency spectrum of heart rate variability to assess the autonomic tone of a patient.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status. Patients with low ejection fraction may be more susceptible to hemodynamic intolerance to ventricular pacing. Therefore, an indication of ejection fraction may be used in combination with an indication of the level of change in autonomic tone induced by ventricular pacing to evaluate ventricular pacing intolerance.

IMD 16 may also include one or more sensors 87 separate from electrodes 40, 42, 48, 50, 58, 62 and 66. Via a signal generated by sensor 87, processor 80 may monitor one or more physiological parameters indicative of cardiac contraction, autonomic tone, heart failure, and/or ejection fraction. Examples of sensors 87 that may generate a signal indicative of cardiac contraction include a intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation changes associated with cardiac contractions. Processor 80 may detect cardiac contractions based on signals from one or more sensors 87, and determine heart rate variability based on the intervals between contractions in a manner similar to determining heart rate variability based on P-P or R-R intervals.

In some examples, processor 80 may monitor a physiological parameter indicative of autonomic tone based on a signal provided by one or more sensors 87 both while signal generator 84 delivers ventricular pacing and also while signal generator 84 does not deliver ventricular pacing. Processor 80 may analyze values of a sensed parameter obtained in conjunction with and without ventricular pacing to assess a level of change in autonomic tone induced by ventricular pacing. Examples of physiological parameters indicative of autonomic tone and sensors 87 that may be used to monitor these parameters include R-R intervals and heart rate variability sensed via electrodes, e.g., 40, 42, 48, 50, 62, and 66 of leads 18 and 20 and/or housing electrode 58, and pulse amplitude derived from a vascular plethysmography sensor, e.g., a light source and detector in contact with the skin and/or tissue of patient 14.

In some examples, processor 80 may monitor a physiological parameter indicative of autonomic tone based on a signal provided by one or more sensors 87 both while signal generator 84 delivers stimulation according to a first pacing mode and also while signal generator 84 delivers pacing according to a second, different pacing mode. Processor 80 may analyze values of a sensed parameter obtained in conjunction with the first and second pacing modes to assess which pacing mode is appropriate for patient 14. Processor 80 may similar monitor a physiological parameter indicative of autonomic tone while signal generator 84 delivers stimulation according to different values of a pacing interval to assess which pacing interval is appropriate for patient 14.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 may transmit indications of heart rate variability and/or autonomic tone to programmer 24 via telemetry module 88. For example, processor 80 may store information indicative of a level of change in autonomic tone induced by ventricular pacing and/or a level of automatic tone associated with a pacing mode within memory 82. Upon interrogation by programmer 24, processor 80 may control telemetry module 88 to transmit the information indicative of a level of change in autonomic tone induced by ventricular pacing and/or a level of automatic tone associated with a pacing mode stored in memory 82. As another example, telemetry module 88 may transmit raw signals, e.g., electrogram signals, to programmer 24. Programmer 24 may, in turn, perform signal processing to determine a level of change in autonomic tone induced by ventricular pacing and/or a level of automatic tone associated with a pacing mode. Programmer 24 may also transmit the determined level of change in autonomic tone induced by ventricular pacing and/or a level of automatic tone associated with a pacing mode back to IMD 16, e.g., to allow IMD 16 to make a programming change and/or or store one or more indications of determined changes in and/or levels of autonomic tone within memory 82.

In examples in which processor 80 determines a level of change in autonomic tone induced by ventricular pacing, telemetry module 88 may transmit a notification, e.g., to programmer 24, if the level of change exceeds a threshold. For example, processor 80 may determine whether the level of change in autonomic tone exceeds a threshold value, e.g., a threshold increase in sympathetic and/or decrease in parasympathetic tone. Memory 82 may store one or more threshold values.

Processor 80 may suggest an action to a user of programmer 24, e.g., patient 14 or a clinician, via telemetry module 88 based on a level of change in autonomic tone induced by ventricular pacing. For example, processor 80 may suggest repositioning one or more of leads 18, 20, and 22, upgrading to a cardiac resynchronization (CRT) enabled IMD, and/or decreasing use of ventricular pacing based on an analysis of the level of change in autonomic tone induced by ventricular pacing, e.g., in combination with analysis of values of other physiological and/or system parameters.

Repositioning one or more of leads 18, 20, and 22 may allow patient 14 to better tolerate ventricular pacing. As one example, repositioning RV lead 18 away from the apex of heart 12 may allow patient 14 to better tolerate RV pacing. Memory 82 may store information regarding the positions of leads 18, 20, and 22 and/or responses to previous requests to reposition leads 18, 20, and/or 22. Additionally or alternatively, electrical sensing module 86 and/or sensor 87 may monitor one or more parameters that may provide an indication of whether the positioning of leads 18, 20, and 22 is appropriate. Processor 80 may suggest repositioning one or more of leads 18, 20, and 22 to a user of programmer 24 via telemetry module 88 based on an analysis of the level of change in autonomic tone induced by ventricular pacing, e.g., in combination with analysis of values of other physiological and/or system parameters. A clinician or other user may reposition a lead that delivers ventricular pacing from IMD 16 to the patient 14 based on the suggestion. As one example, the clinician may move RV lead 18 away from the apex of heart 12.

As another example, processor 80 may assess upgrading to an IMD configured for CRT and/or implanted an LV lead 22 based on the level of change in autonomic tone induced by ventricular pacing. For example, if IMD 16 is not configured to deliver CRT, or is not coupled to an LV lead 22, processor 80 may analyze the level of change in autonomic tone induced by ventricular pacing and, optionally, values of other physiological parameters collected by electrical sensing module 86 and/or sensor 87 to determine whether an update to an IMD configured to CRT and/or implantation of an LV lead is appropriate. Processor 80 may provide a suggestion regarding such an upgrade to a user of programmer 24 via telemetry module 88.

Processor 80 may also suggest modifying therapy delivery via telemetry module 88 and programmer 24, e.g., minimizing RV pacing, based on a level of change in autonomic tone induced by ventricular pacing. For example, processor 80 may suggest modified therapy parameter values and/or programs to a user of external programmer 24 via telemetry module 88. As one example, processor 80 may suggest increasing an AV, A-RV, or A-LV delay based on a level of change in autonomic tone induced by ventricular pacing. Telemetry module 88 may receive an acceptance of the modified therapy parameter values and/or programs from the user of programmer 24 via telemetry module 88. In response to the acceptance, processor 80 may control signal generator 84 to deliver the modified therapy. Processor 80 may suggest modifying therapy delivered via IMD 16 if the level of change in autonomic tone induced by ventricular pacing is not significant enough to suggest upgrading to an IMD configured for CRT. As another example, processor 80 may suggest modifying therapy delivered via IMD 16 until an upgrade to an IMD configured for CRT may be performed.

In some examples, processor 80 may automatically change the therapy delivered by signal generator 82 based on the level of change in autonomic tone induced by ventricular pacing. For example, processor 80 may control signal generator 82 to modify therapy delivery to patient 14 if the level of change in autonomic tone induced by ventricular pacing exceeds a threshold value. The therapy modification may include reprogramming of therapy parameter values and/or therapy programs. For example, processor 80 may modify one or more therapy parameter values and/or therapy programs, e.g., stored in memory 82, and control signal generator 84 to deliver therapy according to the reprogrammed therapy parameter values and/or programs. As one example, processor 80 may reprogram therapy delivery by signal generator 84 to decrease the usage of ventricular pacing. For example, processor 80 may modify an AV, A-RV, or A-LV delay, which may result in fewer ventricular depolarizations that are paced. As previously described, telemetry module 88 may send therapy modifications to a user of external programmer 24 for approval rather than automatically implement the changes.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

Figure 5:
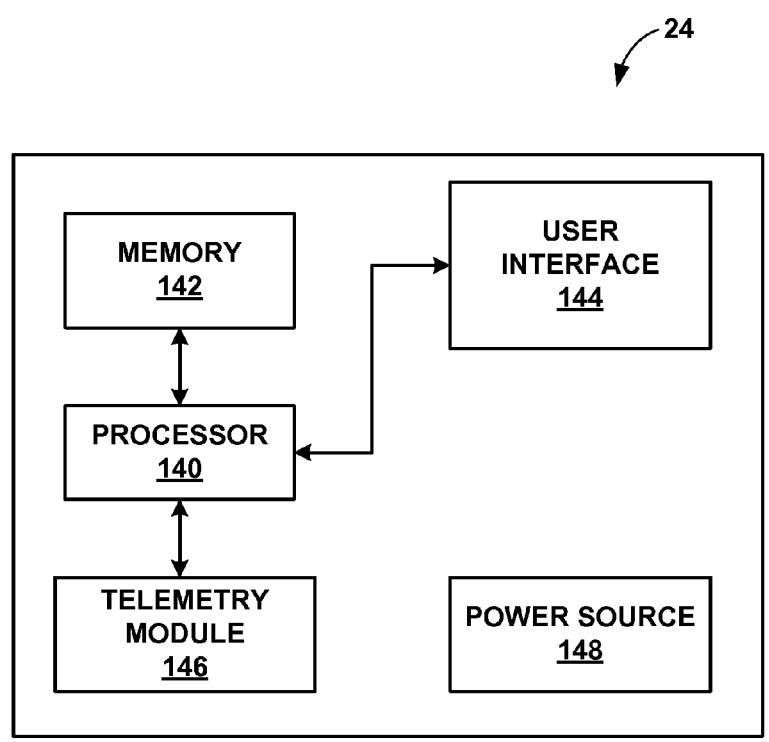
FIG. 5 is block diagram of an example external programmer that facilitates user communication with the IMD.

FIG. 5 is block diagram of an example programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. The clinician may interact with programmer 24 via user interface 144 which may include display to present a graphical user interface to a user, and a keypad or another mechanism for receiving input from a user.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 142 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 may be configured to provide some or all of the functionality ascribed to processor 80 of IMD 16 herein. For example, processor 140 may receive indications of cardiac depolarizations or contractions, a signal from one or more sensors 87, or information regarding autonomic tone or heart rate variability from IMD 16 via telemetry module 146. In some examples, processor 140 may control suspension of ventricular pacing by IMD 16 for evaluation of the tolerance of the ventricular pacing. Processor 140 may determine whether ventricular pacing is tolerated, and provide an alert, suggest a system or therapy change, or automatically change the therapy, as described above with respect to IMD 16 and processor 80.

Figure 6:
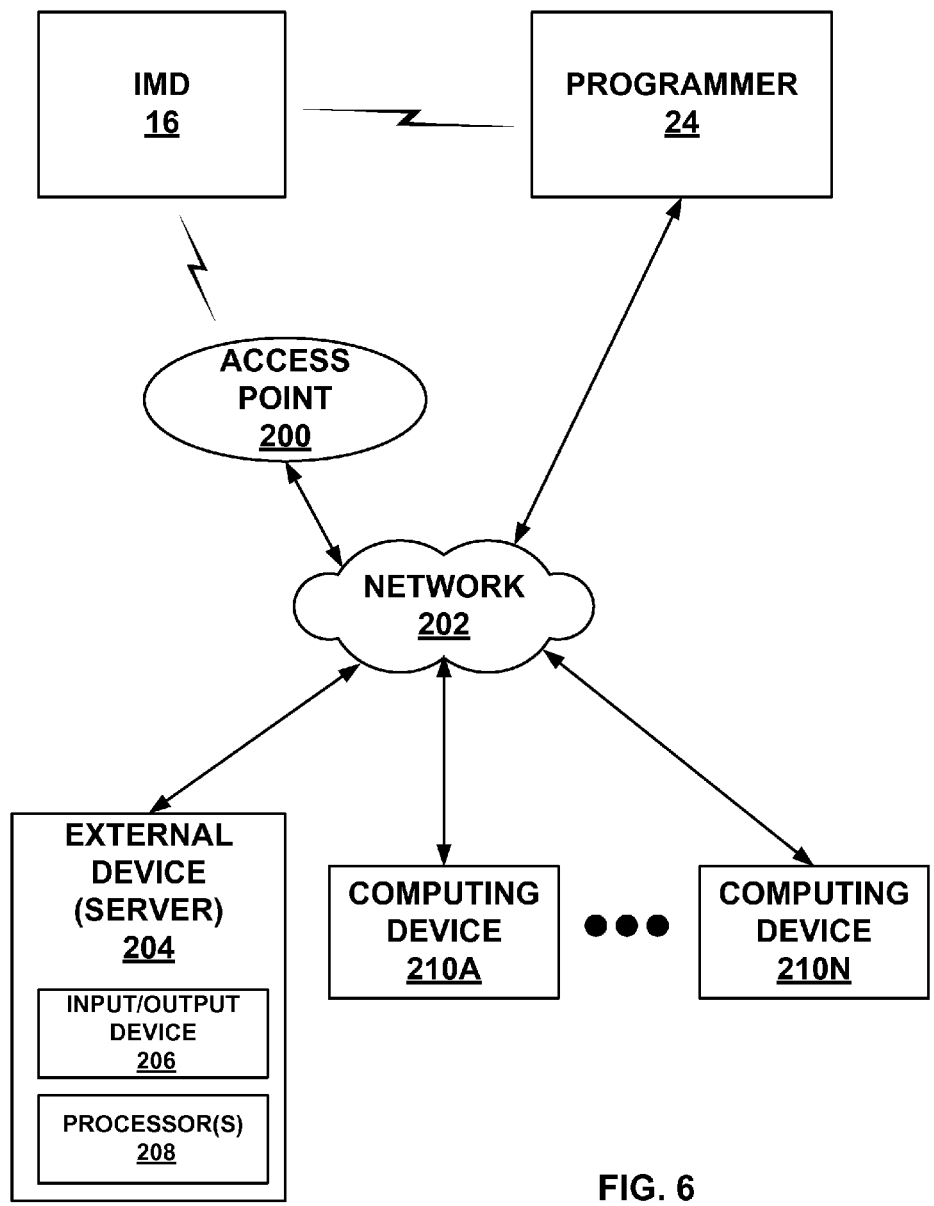
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210 are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 21 0A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 208 of server 204 may be configured to provide some or all of the functionality ascribed to processor 80 of IMD 16 herein. For example, processor 206 may receive indications of cardiac depolarizations or contractions, a signal from one or more sensors 87, or information regarding autonomic tone or heart rate variability from IMD 16 via access point 200 or programmer 24 and network 202. Processor 206 may determine whether ventricular pacing is tolerated, and provide an alert, suggest a system or therapy change, or automatically change the therapy delivered by IMD 16 via network 202 and programmer 24 or access point 200, as described above with respect to IMD 16 and processor 80. Processor 208 may provide an alert or suggest a therapy change by sending a notification to one or more computing devices 210 via network 202. In some examples, server 204 relays an alert or suggestion provided by one or more of IMD 16 or programmer 24 to one or more of computing devices 210 via network 202.

Figure 7:
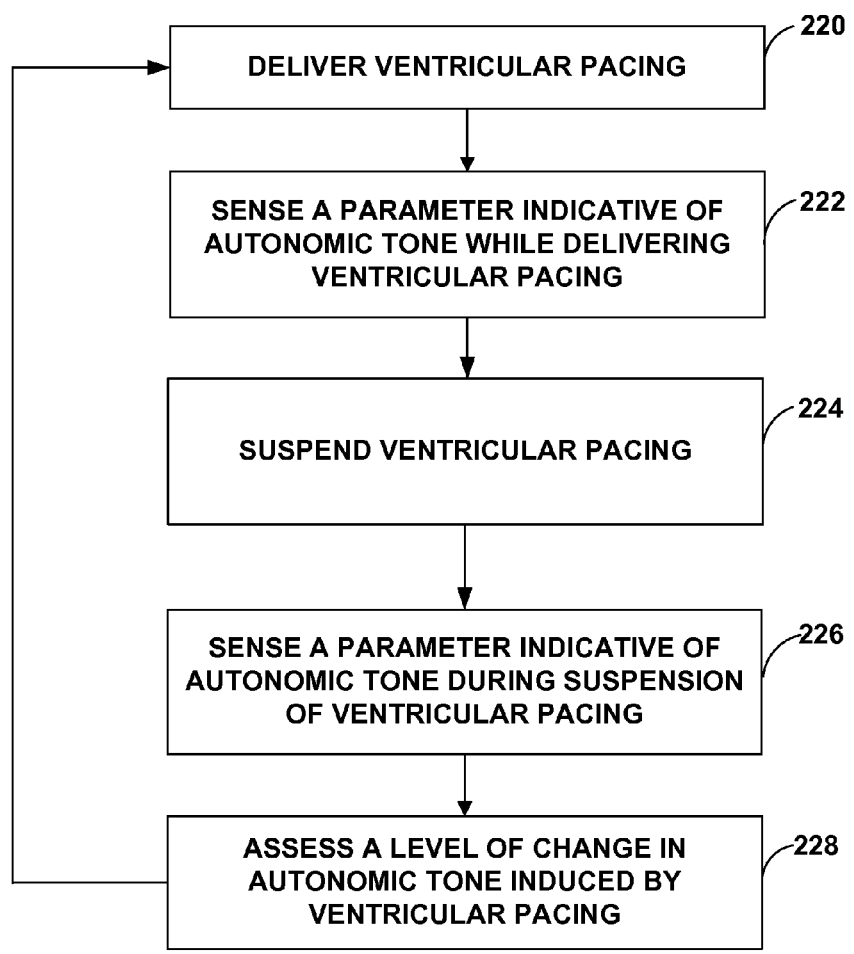
FIG. 7 is a flow diagram of an example method of assessing a level of change in autonomic tone in a patient induced by ventricular pacing.

FIG. 7 is a flow diagram of an example method of assessing a level of change in autonomic tone in a patient induced by ventricular pacing. The functionality described with respect to FIG. 7 as being provided a particular processor or device may, in other examples, be provided by any one or more of the processors or devices described herein.

Signal generator 84 of IMD 16 delivers ventricular pacing to heart 12 of patient 14, e.g., to right ventricle 28 (220). Electrical sensing module 86 and/or sensor 87 senses a parameter indicative of autonomic tone while signal generator 84 delivers ventricular pacing (222). As one example, electrical sensing module 86 detects ventricular depolarizations. Processor 80 may determine R-R intervals, and process the R-R intervals to obtain information regarding heart rate variability, which may provide an indication of autonomic tone.

Processor 80 then controls signal generator 84 to suspend delivery of the ventricular pacing (224). Electrical sensing module 86 and/or sensor 87 may then sense a parameter indicative of autonomic tone when signal generator 84 is not delivering ventricular pacing to heart 12, e.g., when signal generator 84 does not output a signal (226). Based on the values of the sensed parameter recorded while signal generator 84 delivers ventricular pacing and while signal generator 84 does not deliver ventricular pacing, processor 80 may determine a level of change in autonomic tone induced by ventricular pacing (228). As one example, a decrease in heart rate variability in response to ventricular pacing may indicate an undesired change in autonomic tone induced by the ventricular pacing.

In some examples, processor 80 may store information indicative of a level of change in autonomic tone induced by ventricular pacing within memory 82. Upon interrogation by programmer 24, processor 80 may control telemetry module 88 to transmit the information indicative of a level of change in autonomic tone induced by ventricular pacing stored in memory 82. As another example, telemetry module 88 may transmit raw signals, e.g., electrogram signals, to programmer 24. Programmer 24 may, in turn, perform signal processing to determine a level of change in autonomic tone induced by ventricular pacing.

In examples in which processor 80 determines a level of change in autonomic tone induced by ventricular pacing, telemetry module 88 may transmit a notification, e.g., to programmer 24, if the level of change exceeds a threshold. For example, processor 80 may determine whether the level of change in autonomic tone exceeds a threshold value, e.g., a threshold increase in sympathetic and/or decrease in parasympathetic tone. Memory 82 may store one or more threshold values.

Processor 80 may suggest an action to a user of programmer 24, e.g., patient 14 or a clinician, via telemetry module 88 based on a level of change in autonomic tone induced by ventricular pacing. For example, processor 80 may suggest repositioning one or more of leads 18, 20, and 22 (FIG. 1), implanting an LV lead 22, upgrading to a cardiac resynchronization (CRT) enabled IMD, and/or decreasing use of ventricular pacing based on an analysis of the level of change in autonomic tone induced by ventricular pacing, e.g., in combination with analysis of values of other physiological and/or system parameters.

In some examples, processor 80 may automatically change the therapy delivered by signal generator 82 based on the level of change in autonomic tone induced by ventricular pacing. For example, processor 80 may control signal generator 82 to modify therapy delivery to patient 14 if the level of change in autonomic tone induced by ventricular pacing exceeds a threshold value. The therapy modification may include reprogramming of therapy parameter values and/or therapy programs. For example, processor 80 may modify one or more therapy parameter values and/or therapy programs, e.g., stored in memory 82, and control signal generator 84 to deliver therapy according to the reprogrammed therapy parameter values and/or programs. As one example, processor 80 may reprogram therapy delivery by signal generator 84 to decrease the usage of ventricular pacing. For example, processor 80 may modify a delay time following atrial activity that signal generator 84 uses for timing ventricular pacing signals, e.g., an A-V, A-RV, or A-LV delay. As previously described, telemetry module 88 may send therapy modifications to a user of external programmer 24 for approval rather than automatically implement the changes.

Figure 8:
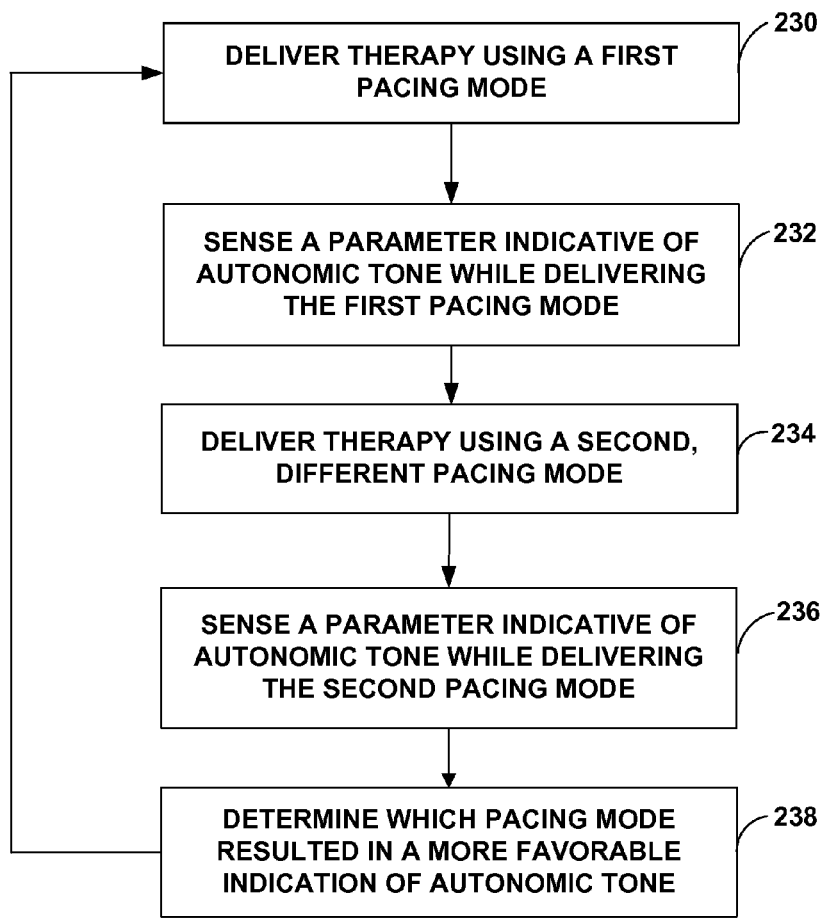
FIG. 8 is a flow diagram of an example method of comparing two different pacing modes based on indications of autonomic tone.

FIG. 8 is a flow diagram of an example method of comparing two different pacing modes based on indications of autonomic tone. The functionality described with respect to FIG. 8 as being provided a particular processor or device may, in other examples, be provided by any one or more of the processors or devices described herein.

A method for evaluating the trade-offs between increased A-V intervals and decreased ventricular pacing may be clinically useful. In some patients, increased A-V intervals and/or increased ventricular pacing may have a detrimental impact on autonomic tone. Comparing values indicative of autonomic tone recorded when IMD 16 delivers therapy to patient 14 using a first pacing mode and a second, different pacing mode may allow IMD 16 to evaluate which pacing mode in appropriate for patient 14. The first and second pacing modes may include different A-V intervals and/or amounts or types of ventricular pacing.

Signal generator 84 of IMD 16 delivers therapy to patient 14 using a first pacing mode, e.g., an atrial-based pacing mode (230). The atrial-based pacing mode may allow intrinsic A-V conduction. The atrial-based pacing mode may also provide back-up ventricular pacing. For example, if A-V conduction is transiently lost, e.g., an intrinsic ventricular depolarization is not detected between consecutive atrial-paced events on one or a limited number of occurrences, the atrial-based pacing mode may deliver ventricular pacing. If A-V conduction is more persistently lost, e.g., an intrinsic ventricular depolarization is not detected between consecutive atrial-paced events a threshold number of times, IMD 16 may switch to a pacing mode that includes ventricular pacing, e.g., a dual chamber pacing mode that delivers atrial and ventricular pacing.

Electrical sensing module 86 and/or sensor 87 senses a parameter indicative of autonomic tone while signal generator 84 delivers therapy using the first pacing mode (232). As one example, electrical sensing module 86 detects ventricular depolarizations. Processor 80 may determine R-R intervals, and process the R-R intervals to obtain information regarding heart rate variability, which may provide an indication of autonomic tone.

Processor 80 then controls signal generator 84 to deliver therapy to patient 14 using a second, different pacing mode, e.g., a dual chamber pacing mode that delivers atrial and ventricular pacing (234). The dual chamber pacing mode may deliver ventricular pacing based on a programmed A-V interval. For example, if electrical sensing module 86 does not detect an intrinsic depolarization prior to expiration of the programmed AV interval, signal generator 84 delivers a ventricular pacing signal. The dual chamber pacing mode may not allow longer, intrinsic AV intervals that may be allowed with atrial-based pacing modes but may include an increase amount of ventricular pacing compared to atrial-based pacing modes.

Electrical sensing module 86 and/or sensor 87 may then sense a parameter indicative of autonomic tone when signal generator 84 is delivering therapy according to the second pacing mode (236). Based on the values of the sensed parameter recorded while signal generator 84 delivers therapy according to the first pacing mode and while signal generator 84 delivers therapy according to the second pacing mode, processor 80 may determine which pacing mode resulted in a more favorable balance of autonomic tone (238). As one example, the pacing mode that resulted in higher values of heart rate variability may provide a more favorable balance of autonomic tone.

In some examples, processor 80 may store information indicative of a level of autonomic tone associated with the first and/or second pacing mode within memory 82. Upon interrogation by programmer 24, processor 80 may control telemetry module 88 to transmit the information indicative of a level of autonomic tone stored in memory 82. As another example, telemetry module 88 may transmit raw signals, e.g., electrogram signals, to programmer 24. Programmer 24 may, in turn, perform signal processing to determine a level of autonomic tone for each of the first and second pacing modes.

In examples in which processor 80 determines a level of autonomic tone for each of the first and second pacing modes, telemetry module 88 may transmit a notification, e.g., to programmer 24, of which pacing mode is more appropriate for patient 14. Processor 80 may suggest an action to a user of programmer 24, e.g., patient 14 or a clinician, via telemetry module 88 based on while pacing mode is associated with a more favorable balance of autonomic tone. For example, processor 80 may suggest predominately using the pacing mode associated with the more favorable balance of autonomic tone over the other, less favorable pacing mode.

In some examples, processor 80 may automatically change the therapy delivered by signal generator 82 based on which pacing mode is associated with the more favorable balance of autonomic tone. In other examples, telemetry module 88 may send therapy modifications to a user of external programmer 24 for approval rather than automatically implement the changes.

IMD 16 may periodically re-check autonomic balance information between the first and second pacing modes using the method described with respect to FIG. 8. The amount of time autonomic tone data is sampled and averaged with each pacing mode may be programmable.

Although the description of FIG. 8 primarily refers to comparing an atrial-based pacing mode to a dual chamber pacing mode, other types of pacing modes may also be compared. For example, a biventricular pacing mode may be compared to an atrial-based pacing mode and/or a ventricular pacing mode that delivers pacing to a single ventricle.

In some examples, instead of or in addition to assessing two or more pacing modes, any one or more of the processors or devices described herein may assess a plurality of different values for a pacing interval. In examples in which IMD 16 comprises a single chamber pacemaker that delivers ventricular pacing, IMD 16 may compare different ventricular pacing rates. An increased pacing rate may lead to an increase in sympathetic and/or decrease in parasympathetic tone due to the increase in the frequency of ventricular pacing. IMD 16 may start with a lower pacing rate, e.g., 40 beats per minute, and sample heart rate variability data while delivering therapy at the lower pacing rate. IMD 16 may increase the pacing rate to a higher pacing rate, e.g., 60 beats per minute, and sample heart rate variability data while delivering therapy at the higher pacing rate. If there is no deleterious effect in heart rate variability upon increasing the pacing rate, IMD 16 may select the higher pacing rate for therapy delivery. The higher pacing rate may be within an allowed heart rate range established by a clinician. In other examples, a different indication of autonomic tone may be used in addition to or in place of heart rate variability.

In some examples, IMD 16 may compare different values of the programmable A-V interval for a pacing mode. IMD 16 may sample heart rate variability data or other data indicative of autonomic tone when each of the different values of the programmable A-V interval is used to deliver therapy. The A-V interval value which corresponds to the highest heart rate variability or otherwise corresponds to the most favorable indication of autonomic balance may be selected for use with chronic therapy delivery. This may be an A-V interval value at which there is no right ventricular pacing, some ventricular pacing, or even complete ventricular pacing. IMD 16 may program an upper allowed A-V interval value based upon analysis of data indicative of autonomic tone.

Various examples have been described. These and other examples are within the scope of the following claims.

The invention claimed is:

1. A method comprising:
sensing a parameter indicative of autonomic tone during a first period in which a medical device delivers ventricular pacing to a patient during a first plurality of consecutive R-R intervals;
sensing the parameter indicative of autonomic tone during a second period in which the medical device does not deliver ventricular pacing to the patient during a second plurality of consecutive R-R intervals different than the first plurality of consecutive R-R intervals; and
assessing, by one or more processors, a level of change in autonomic tone in the patient induced by ventricular pacing based on values of the sensed parameter during the first and second periods.

2. The method of claim 1, wherein the sensed parameter comprises heart rate variability.

3. The method of claim 1, further comprising storing an indication of the level of change in autonomic tone within the medical device.

4. The method of claim 1, further comprising transmitting an indication of the level of change in autonomic tone to an external device.

5. The method of claim 1, further comprising sending a notification to a user if the level of change in autonomic tone exceeds a threshold.

6. The method of claim 1, further comprising modifying how the medical device delivers therapy to the patient based on the level of change in autonomic tone.

7. The method of claim 6, wherein modifying how the medical device delivers therapy comprises modifying a delay time following atrial activity that the medical device uses for timing delivery of ventricular pacing signals.

8. The method of claim 6, wherein modifying how the medical device delivers therapy comprises reprogramming the medical device to decrease usage of ventricular pacing.

9. The method of claim 6, wherein modifying how the medical device delivers therapy comprises repositioning a lead that delivers ventricular pacing from the medical device to the patient.

10. The method of claim 9, wherein repositioning the lead comprises moving the lead away from an apex of a heart of the patient.

11. The method of claim 1, wherein the medical device is not configured for cardiac resynchronization therapy, further comprising assessing upgrading to a medical device configured for cardiac resynchronization therapy based on the level of change in autonomic tone.

12. The method of claim 11, wherein upgrading the medical device comprises attaching a left ventricular lead to the medical device.

13. The method of claim 1, wherein the ventricular pacing comprise right ventricular pacing.

14. The method of claim 1, wherein the medical device comprises an implantable medical device.

15. A system comprising:
a medical device configured to deliver ventricular pacing to a patient during a first period of a first plurality of consecutive R-R intervals, and configured to not deliver ventricular pacing to the patient during a second period of a second plurality of consecutive R-R intervals different than the first plurality of consecutive R-R intervals;
a sensor configured to sense a parameter indicative of autonomic tone during each of the first and second periods; and
a processor configured to assess a level of change in autonomic tone in the patient induced by ventricular pacing based on values of the sensed parameter during the first and second periods.

16. The system of claim 15, wherein the sensor is configured to sense heart rate variability.

17. The system of claim 15, further comprising a memory configured to store an indication of the level of change in autonomic tone.

18. The system of claim 15, further comprising an external device configured to receive an indication of the level of change in autonomic tone.

19. The system of claim 15, further comprising a telemetry module configured to send a notification to a user if the level of change in autonomic tone exceeds a threshold.

20. The system of claim 15, wherein the medical device is configured to deliver a modified therapy to the patient based on the level of change in autonomic tone.

21. The system of claim 20, wherein the medical device is configured to use a modified delay time following atrial activity for timing delivery of ventricular pacing.

22. The system of claim 20, wherein the medical device is configured to deliver the modified therapy with decreased usage of ventricular pacing.

23. The system of claim 15, further comprising a lead configured to deliver ventricular pacing signals from the medical device to the patient, wherein the lead is repositioned based on the level of change in autonomic tone.

24. The system of claim 15, wherein the medical device is not configured for cardiac resynchronization therapy, and wherein the processor is configured to assess, based on the level of change in autonomic tone, upgrading to a medical device configured for cardiac resynchronization therapy.

25. The system of claim 24, wherein upgrading the medical device comprises attaching a left ventricular lead to the medical device.

26. The system of claim 15, wherein the sensor comprises one or more electrodes coupled to the medical device via one or more leads.

27. The system of claim 15, wherein the ventricular pacing comprises right ventricular pacing.

28. The system of claim 15, wherein the medical device comprises an implantable medical device.

29. A medical device comprising:
a signal generator configured to deliver ventricular pacing to a patient during a first period of a first plurality of consecutive R-R intervals, and configured to not deliver ventricular pacing to the patient during a second period of a second plurality of consecutive R-R intervals different than the first plurality of consecutive R-R intervals;
a sensor configured to sense a parameter indicative of autonomic tone during each of the first and second periods; and
a processor configured to assess a level of change in autonomic tone in the patient induced by ventricular pacing based on values of the sensed parameter during the first and second periods.

30. The medical device of claim 29, wherein the sensor is configured to sense heart rate variability.

31. The medical device of claim 29, further comprising a memory configured to store an indication of the level of change in autonomic tone.

32. The medical device of claim 29, further comprising a telemetry module configured to transit an indication of the level of change in autonomic tone to an external device.

33. The medical device of claim 32, wherein the telemetry module is configured to send a notification to a user if the level of change in autonomic tone exceeds a threshold.

34. The medical device of claim 29, wherein the signal generator is configured to deliver a modified therapy to the patient based on the level of change in autonomic tone.

35. The medical device of claim 34, wherein the signal generator is configured to use a modified delay time following atrial activity for timing delivery of ventricular pacing.

36. The medical device of claim 34, wherein the processor is configured to control the signal generator to decrease usage of ventricular pacing.

37. The medical device of claim 29, further comprising a lead configured to deliver ventricular pacing signals from the signal generator to the patient, wherein the lead is repositioned based on the level of change in autonomic tone.

38. The medical device of claim 29, wherein the medical device is not configured for cardiac resynchronization therapy, and wherein the processor is configured to assess upgrading to a medical device configured for cardiac resynchronization therapy based on the level of change in autonomic tone.

39. The medical device of claim 38, wherein upgrading the medical device comprises attaching a left ventricular lead to the medical device.

40. The medical device of claim 29, wherein the sensor comprises one or more electrodes coupled to the medical device via one or more leads.

41. The medical device of claim 29, wherein the ventricular pacing comprise right ventricular pacing.

42. The medical device of claim 29, wherein the medical device comprises an implantable medical device.

43. A system comprising:
   means for sensing a parameter indicative of autonomic tone during a first period in which a medical device delivers ventricular pacing to a patient during a first plurality of consecutive R-R intervals;
   means for sensing the parameter indicative of autonomic tone during a second period in which the medical device does not deliver ventricular pacing to the patient during a second plurality of consecutive R-R intervals different than the first plurality of consecutive R-R intervals; and
   means for assessing a level of change in autonomic tone in the patient induced by ventricular pacing based on values of the sensed parameter during the first and second periods.

44. A non-transitory computer-readable storage medium comprising instructions that cause a processor to:
   sense a parameter indicative of autonomic tone during a first period in which a medical device delivers ventricular pacing to a patient during a first plurality of consecutive R-R intervals;
   sense the parameter indicative of autonomic tone during a second period in which the medical device does not deliver ventricular pacing to the patient during a second plurality of consecutive R-R intervals different than the first plurality of consecutive R-R intervals; and
   assess a level of change in autonomic tone in the patient induced by ventricular pacing based on values of the sensed parameter during the first and second periods.

* * * * *